United States Patent
Schlarb et al.

(10) Patent No.: US 8,538,122 B2
(45) Date of Patent: Sep. 17, 2013

(54) LOCALIZATION OF A VALID AREA OF A BLOOD SMEAR

(75) Inventors: Timo Schlarb, Kirschroth (DE);
Stephan Rupp, Erlangen (DE);
Thorsten Zerfass, Nuremberg (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 100 days.

(21) Appl. No.: 13/344,624

(22) Filed: Jan. 6, 2012

(65) Prior Publication Data

US 2012/0155739 A1  Jun. 21, 2012

Related U.S. Application Data

(63) Continuation of application No. PCT/EP2010/060082, filed on Jul. 13, 2010.

(30) Foreign Application Priority Data

Jul. 20, 2009 (DE) .................. 10 2009 033 927

(51) Int. Cl.
*G06K 9/00* (2006.01)

(52) U.S. Cl.
USPC ........... 382/133; 382/134; 382/224; 382/225; 382/181

(58) Field of Classification Search
USPC ................. 382/133, 134, 224, 225
See application file for complete search history.

(56) References Cited

U.S. PATENT DOCUMENTS

| 4,362,386 | A   |   | 12/1982 | Matsushita et al. |
| 4,702,595 | A   |   | 10/1987 | Mutschler et al. |
| 5,703,959 | A   | * | 12/1997 | Asano et al. ............... 382/133 |
| 6,330,350 | B1  | * | 12/2001 | Ahn et al. ................... 382/134 |
| 7,282,179 | B2  | * | 10/2007 | Iwaki et al. ................. 422/422 |
| 2007/0014460 | A1 |  | 1/2007 | Kuziela et al. |

FOREIGN PATENT DOCUMENTS

| DE | 30 43 530 A1 | 9/1981 |
| DE | 103 53 785 B4 | 5/2006 |

OTHER PUBLICATIONS

Theml et al.,"The Blood Smear and its Evaluation (Differential Blood Count)", Thieme Verlag, Stuttgart, New York, 2002, pp. 17-19.
Official Communication issued in International Patent Application No. PCT/EP2010/060082, mailed on Oct. 11, 2010.
Otsu, "A Threshold Selection Method from Gray-Level Histograms", IEEE Transactions on Systems, Man, and Cybernetics, vol. SMC-9, No. 1, Jan. 1979, pp. 62-66.
Mues-Hinterwaeller et al., "Detektion and berandungsgenaue Segmentierung von Erythrozyten", Jan. 1, 2005, pp. 1-5.

(Continued)

*Primary Examiner* — Tom Y Lu
(74) *Attorney, Agent, or Firm* — Keating & Bennett, LLP

(57) ABSTRACT

Automated localization of a valid area of a blood smear and, thus, localization requiring less effort and being more objective is enabled in that a picture of the blood smear pixels are classified at least into first pixels, which represent blood cells, and second pixels, which do not represent the blood cells, and the valid area is then found on the basis of a local frequency of pixel clusters of at least $A_{min}$ first pixels, $A_{min}$ being a minimum threshold for a number of first pixels of a pixel cluster, and a local average size of the pixel clusters for laterally distributed areas of the blood smear.

13 Claims, 7 Drawing Sheets

(56) References Cited

OTHER PUBLICATIONS

Xiong et al., "Automatic Working Area Classification in Peripheral Blood Smears without Cell Central Zone Extraction", 30th Annual International IEEE EMBS Conference, Aug. 20-24, 2008, pp. 4074-4077.

Xiong et al., "Automatic Working Area Classification in Peripheral Blood Smears Using Spatial Distribution Features Across Scales", 19th International Conference on Pattern Recognition, Dec. 8-11, 2008, pp. 1-4.

Angulo et al., "Automated Detection of Working Area of Peripheral Blood Smears Using Mathematical Morphology", Analytical Cellular Pathology, vol. 25, Elsevier Science, Jan. 1, 2003, pp. 37-49.

\* cited by examiner

LOCALIZATION OF A VALID AREA OF A BLOOD SMEAR

CROSS-REFERENCE TO RELATED APPLICATIONS

This application is a continuation of copending German Application No. 102009033927.2, filed Jul. 20, 2009, which is incorporated herein by reference in its entirety.

The present invention relates to localization of a valid area of a blood smear, such as on a microscope slide, for example.

Methods of computer-assisted diagnosis (CAD) support doctors in making their decisions in terms of diagnosis. The aim of these methods is to improve quality of diagnoses, on the one hand, and to replace expensive double reports made by a second doctor, on the other hand. In the last few years, CAD systems were developed for diagnosing skin cancer, breast cancer and for diagnosing the blood count, among others.

For medical diagnostics, blood is an indispensable indicator of a wide variety of diseases, i.e. of diseases that are transmissible via blood, via parasites, and of sexually transmissible diseases. For routine examinations, blood is typically analyzed automatically by means of flow cytometry or by utilization of fluorescence activated cell sorting (FACS). Unfortunately, said automatic methods do not provide satisfactory results in 30% to 40% of analyses. Therefore, subsequent visual testing of the blood is of vital importance in these cases. Moreover, there are many cases of application where visual testing of a blood smear is necessitated, even if there is no suspicion of pathology.

A "blood smear" is understood to mean a method of preparing blood for, e.g., microscopic examination, or the result of this method. The process of preparing a blood smear is shown in FIG. 6 by way of example. Blood smears are used, e.g., for cytological and hematological examinations of blood cells, e.g. for counting leucocytes, or white blood cells, and for proving the existence of bacteria or parasites in the blood, such as malaria, for example.

As is shown in FIG. 6, the process of preparing a blood smear starts with depositing a drop of blood 900 onto a slide 902, for example by means of a finger prick, as is indicated by the finger 904 (cf. FIG. 6a). The drop of blood 900 is deposited, in particular, in the vicinity of one of the narrow ends of the slide 902. Subsequently, a second slide 906 or a similar, plate-shaped object is placed with its edge upon the slide 902, namely in that part of the slide 902 that is located opposite, via the drop of blood 900, that narrow end of said slide 902 in whose vicinity is located. Subsequently, the slide 906 that is tilted in the direction of the blood is carefully brought close to the drop of blood 900, as is indicated by the arrow 908, until the slide 906 gets into contact with the drop of blood 900 and the blood starts to spread laterally along the edge of the slide 906 (cf. FIG. 6b). Then the slide 906 is tilted further in the direction counter to the direction 910 of the smear, such as to 15° to 40°, as is depicted in FIG. 6c. Subsequently, the blood is spread on the slide 902 in the direction 910 of the smear and away from the nearby narrow edge of the slide 902 in that the slide 906 is brushed over the slide 902 at the angle mentioned, having the blood "in tow", as it were. The result is shown in FIG. 6d: the blood smear 912 on the slide 902. Thus, the blood smear 912 is a thin film of blood on the slide 902. It is dried and possibly subject to coloration, such as to Brehmer coloration or the like, for example. Possibly, fixation is also performed, for example by means of methanol.

In other words, to obtain a blood smear, a small amount of blood is placed on one end of a microscope slide and is spread over the full length thereof. The goal is to obtain a region where the blood cells are spaced sufficiently far apart from one another to be differentiated and/or classified in a targeted manner. This region is frequently referred to as the valid region or the work area. Preparation of such a blood smear may be performed automatically or manually. Unfortunately, blood smear preparation devices are very expensive and thus result in high costs. The consequence is that small or medium-sized laboratories fall back on manual preparation. However, a large amount of skill and experience on the part of a laboratory assistant is necessitated to achieve a good blood smear having a valid region large enough and suitable for examination. Even so, suitable blood smear preparation is not guaranteed and still is repeated frequently. As was already mentioned, once it has been produced, the blood smear may be fully air-dried, and the slide may be wetted with methanol so as to fix the blood smear, whereupon coloration may be performed in order to visualize the blood cells.

The system HemaCAM® for hematology is a computer-assisted diagnostic system, developed at Fraunhofer IIS, for automatic analysis of blood smears for creating a differential blood count.

Reliable recognition and exact segmentation of white blood cells (leucocytes) in colored smears of peripheral blood form the foundation of automatic, image-based creation of a so-called differential blood count in the context of medical laboratory diagnostics (so-called computer-assisted microscopy—CAM). The diversity of the white blood cells occurring in a blood smear, along with their characteristic color distributions and texturing, increases the difficulties in classification within the context of full automation. Automatic detection and segmentation of white blood cells in digital images enables subsequent segmentation—which is precise in terms of boundaries—of the cell nucleus and cell plasma with regard to subsequent classification. A prerequisite for the detection and segmentation and, thus, an essential factor for the validity of the diagnosis is that the blood cells on the slide are evaluated in the valid area.

The valid area on the slide is characterized in that the blood cells are located adjacent to one another, rather than on top of one another, and at almost equal distances. It is only occasionally that the blood cells touch one another; they do not form any cell chains or cell clusters. According to THEML, H., H. DIEM and T. HAFERLACH: *Taschenatlas der Hämatologie*, Thieme Verlag, Stuttgart, New York, 2002, experience has shown that this area is located about 1 cm behind the end of the beard. For a smear having normal leukocyte counts, there are, on average, two to three leucocytes per field of vision when observed with 40-fold object enlargement.

It would therefore be desirable to have a scheme for localizing a valid area of a blood smear that enables automatic localization, so that the examination expenditure may be lowered and the examination results may be rendered easier to compare since they are obtained by user-independent, or objective, criteria.

SUMMARY

According to an embodiment, an apparatus for localizing a valid area of a blood smear may have: a provider for providing at least one picture of the blood smear; a classifier for classifying pixels of the at least one picture at least into first pixels, which represent blood cells, and second pixels, which do not represent the blood cells; a selector for selecting an area of the blood smear as the valid area on the basis of a local frequency of contiguous pixel clusters of at least $A_{min}$ first pixels, $A_{min}$ being a minimum threshold value of a number of first pixels of a pixel cluster, and of a local average size of the pixel clusters for laterally distributed areas of the blood smear.

According to another embodiment, a method of localizing a valid area of a blood smear may have the steps of: providing at least one picture of the blood smear; classifying pixels of the at least one picture at least into first pixels, which represent blood cells, and second pixels, which do not represent the blood cells; selecting an area of the blood smear as the valid area on the basis of a local frequency of contiguous pixel clusters of at least $A_{min}$ first pixels, $A_{min}$ being a minimum threshold value of a number of first pixels of a pixel cluster, and of a local average size of the pixel clusters for laterally distributed areas of the blood smear.

Another embodiment may have a computer program for performing a method of localizing a valid area of a blood smear, which method may have the steps of: providing at least one picture of the blood smear; classifying pixels of the at least one picture at least into first pixels, which represent blood cells, and second pixels, which do not represent the blood cells; selecting an area of the blood smear as the valid area on the basis of a local frequency of contiguous pixel clusters of at least $A_{min}$ first pixels, $A_{min}$ being a minimum threshold value of a number of first pixels of a pixel cluster, and of a local average size of the pixel clusters for laterally distributed areas of the blood smear, wherein the computer program is performed by a processor.

One core idea of the present invention is that automated localization of a valid area of a blood smear and, thus, localization requiring less effort and being more objective is enabled when in a picture of the blood smear pixels are classified at least into first pixels, which represent blood cells, and second pixels, which do not represent the blood cells, and when the valid area is then found on the basis of a local frequency of pixel clusters of at least $A_{min}$ first pixels, $A_{min}$ being a minimum threshold for a number of first pixels of a pixel cluster, and a local average size of the pixel clusters for laterally distributed areas of the blood smear.

In accordance with an embodiment of the present invention, a laterally varying measure of a suitability as a valid area is determined for the laterally distributed areas on the basis of the local frequencies and local average sizes of the pixel clusters, the laterally varying measure depending on the local frequency and on the local average size in accordance with its function, which is either strictly monotonically decreasing for the local frequency and strictly monotonically increasing for the local average size, or strictly monotonically increasing for the local frequency and strictly monotonically decreasing for the local average size, the valid area selected then being that area of the laterally distributed areas wherein the laterally varying measure of suitability as a valid area is extremal.

BRIEF DESCRIPTION OF THE DRAWINGS

Embodiments of the present invention will be detailed subsequently referring to the appended drawings, in which:

FIG. 1 shows an apparatus for localizing a valid area of a blood smear. The apparatus is generally designated by 10. It includes a picture provider 12, a classifier 14, and a selector 16.

DETAILED DESCRIPTION OF THE INVENTION

Figure 1:
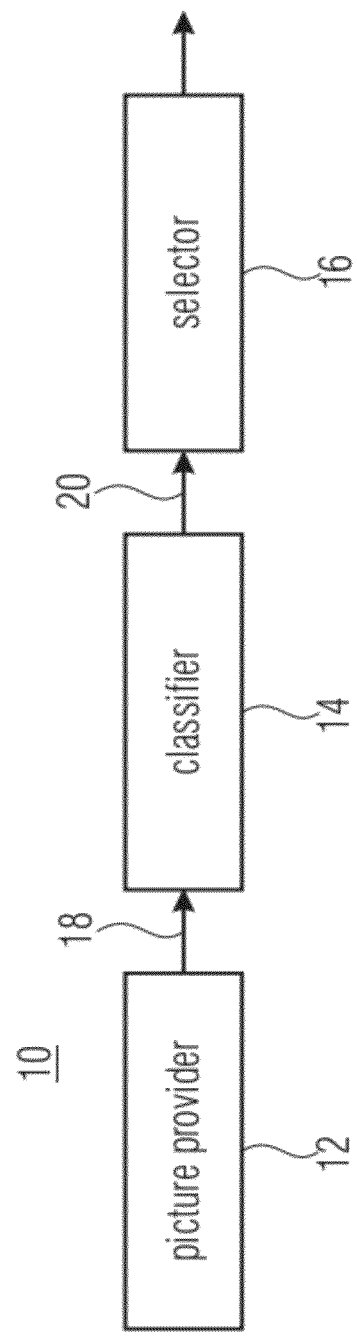
FIG. 1 shows a block diagram of an apparatus for localizing a valid area of a blood smear in accordance with an embodiment.

The picture provider 12 provides at last one picture of the blood smear. Advantageously, the at least one picture fully covers the blood smear. In the embodiments described below, the picture provider 12 provides several pictures of the blood smear, each of which represents only a portion of the blood smear, the portions being laterally offset from one another. They may overlap in some areas, abut one another or be spaced apart from one another. The pictures were obtained, for example, using 10-fold, 20-fold magnification or any magnification in between. The picture provider 12 may be configured such that these pictures have resolutions of 400× 400 pixels, 2000×2000 pixels or any resolution in between.

The picture provider 12 may comprise a data memory 12, for example, such as a non-volatile memory, for example, e.g. a hard disk or a flash memory or the like. The pictures will then have been stored into this memory in advance, such as directly after they were produced. However, the picture provider 12 may also comprise a picture-taking device, such as a microscope having a pixel array, so as to produce the at last one picture.

Thus, the output of the picture provider 12 includes at least one picture 18 of the fluid smear, and the classifier 14 is configured to perform a classification of the pixels for this at least one picture 18. In particular, the classifier 14 is configured to classify and/or categorize the pixels of the at least one picture at least into first pixels, which represent blood cells, and second pixels, which do not represent the blood cells. Thus, the result of the classification may be a binary image or a plurality of binary images resulting from the at least one picture 18 in each case. The classifier 14 may be configured such that it does not distinguish between white and red blood cells. In accordance with one embodiment, which will be explained below, it is also possible, however, that the classifier 14 distinguishes between red and white blood cells and classifies the pixels into first pixels, which represent the red blood cells, and second pixels, which do not represent the red blood cells. The classifier performs the classification for example by subdividing a color space into different areas corresponding to the individual pixel classes, and by classifying the pixels in dependence on the location of the color value of the individual pixels in one of the portions. This will be explained in more detail below.

Thus, the result of the classification on the part of the classifier 14 is a version 20 of the at least one picture 18 of the blood smear, said version 20 being classified by blood cell pixels and non-blood-cell pixels. The selector 16 is configured to select the valid area on the basis of this classified version 20. For example, the classifier 14 and the selector 16 may both be implemented by means of software on a processor.

The selector 16 is configured to select the valid area on the basis of a local frequency of contiguous pixel clusters of at least $A_{min}$ first pixels, $A_{min}$ being a minimum threshold value of a number of first pixels of a pixel cluster, and on the basis of a local average size of the pixel clusters for laterally distributed areas of the blood smear. Advantageously, the laterally distributed areas of the blood smear are distributed along the direction of the blood smear. In accordance with embodiments, which will be described in the following, the laterally distributed areas each correspond to a picture 18, the local frequency then corresponding to the number of pixel clusters in a respective picture, and the local average size corresponding to the average size of the pixel clusters in a respective picture. As will also be described below, the selector 16 may be configured such that it determines the selection of the valid area by means of a measure, or a scalable magnitude, which represents an at least ordinally scaled measure of suitability as a valid area. This measure, or this scalable variable, may depend on the local frequency and the local average size in accordance with a function that is either strictly monotonically decreasing for the local frequency and strictly monotonically increasing for the local average size, or is strictly monotonically increasing for the local frequency and strictly monotonically decreasing for the local average size. Specific examples of this will be provided in the following. However, it is also possible for the selector 16 to determine the selection of the valid area differently than on the basis of the local frequency and the local average size, e.g. on the basis of an evaluation of the track along which the tuples of local frequency and local average size for the laterally distributed areas are located within one plane spanned by an axis for the local frequency and by an axis for the local average size. The various alternatives will be illustrated in more detail by means of FIG. 2.

Figure 2:
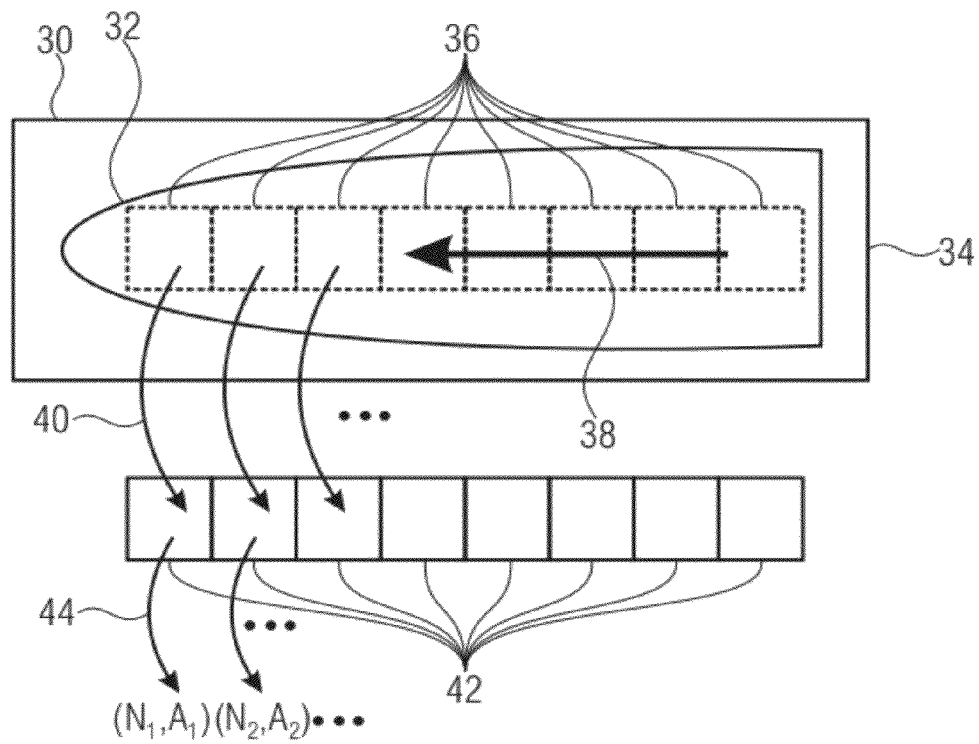
FIG. 2 shows a schematic drawing for illustrating localization of a valid area of a blood smear such as by the apparatus of FIG. 1 in accordance with an embodiment.
Figure 2:
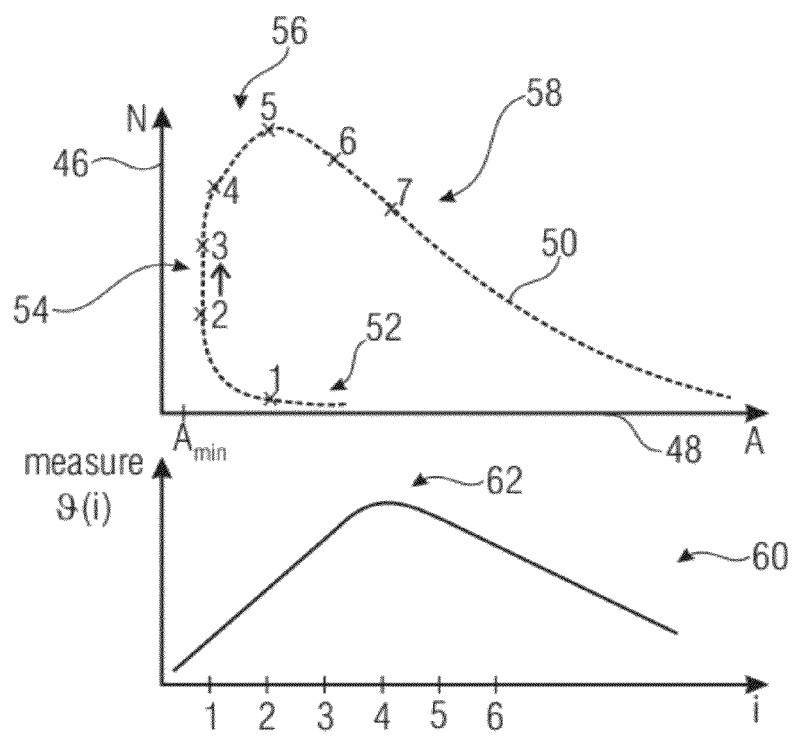

FIG. 2 represents a possible approach in localizing a valid area of a blood smear as may be performed, by way of example, by the apparatus of FIG. 1. FIG. 2 shows a slide 30 having a blood smear 32 on one surface 34 thereof. In accordance with FIG. 2, the picture provider 12 provides, or creates, several pictures 36 of the blood smear 32. As is shown in FIG. 2, the pictures 36 cover different portions of the blood smear 32. Even though in FIG. 2 they are depicted, by way of example, such that they represent non-overlapping, but abutting portions of the blood smear 32, the pictures 36 may just as well overlap and/or may also be spaced apart from one another. As is shown in FIG. 2, the pictures 36 may be mutually offset in the direction of the blood smear 38. However, it is also possible for the pictures 36 to be adjacent at least partly in the direction 38 of the blood smear. In the following it shall be assumed that the pictures 36 are mutually offset, in the direction 38 of the blood smear, such that they may clearly be sequenced with regard to the direction 38 of the blood smear; the indices indicating the picture number are to refer to this sequence in the following. The pictures have such locations on and/or along the blood smear associated with them at which the area shown by the respective picture of the blood smear is located. For example, a moving device moves toward specific locations, so that the pictures are taken at these locations. Or the locations are measured during picture-taking without being used for performing closed-loop or open-loop control on the relative motion between the picture-taker and/or the microscope and slide.

As is indicated by arrows 40, the pixels in the individual pictures 36 are then classified, such as by the classifier 14 of FIG. 1. As was mentioned above, classification may distinguish between first pixels, which represent blood cells, and second pixels, which do not represent the blood cells. The results are classified versions 42 of the pictures 36 on which the pixels representing the blood cells of interest may be distinguished from the other pixels not representing these blood cells. Said classified versions 42 may be binary images, for example. For example, the blood cells of interest may be only the white blood cells, only the red blood cells, or red and white blood cells. For ease of classification, the blood smear 32 typically has been subjected to a suitable colorization process before the pictures 36 were taken, for example; an embodiment of this will be mentioned in the following. The classification may be performed, e.g., on the basis of a subdivision of a color space, such as of the HSV color space, into a first portion and a second portion. Pixels whose color values are in the first portion are then interpreted to represent a blood cell of interest, for example, and pixels whose color values are in the second portion are interpreted as representing no blood cell of interest.

As is indicated by arrows 44, a tuple or a pair of values is determined to be associated with each of the images 42, namely a local frequency and/or a local number of pixel clusters of such pixels in the respective image that represent a blood cell of interest, and an average size of said pixel clusters. As is shown in FIG. 2, two values, namely a local frequency $N_i$ and a local average size $A_i$ thereby result for each image i of the images 42. A specific embodiment of determining $N_i$ and $A_i$ will be provided below. At any rate, it is possible for the selector 16 to count, during determination 44, only the contiguous pixel clusters which consist of a number of mutually adjacent blood cell pixels, said number exceeding a predetermined minimum number $A_{min}$. The local average size $A_i$, for example, is determined by the selector 16 only for said pixel clusters. For example the number of pixels of a pixel cluster is used as a measure of the size. In order to average the frequency distribution of the sizes of the pixel clusters in the respective local area or image 42, any central tendency such as the mean value, the mode, or the median, for example, may be used. The pictures are provided, e.g., with a 10-fold or a 20-fold magnification or any magnification in between at a resolution of 400×400 pixels, 2000×2000 pixels or any resolution in between, $A_{min}$ ranging from 10, inclusively, to 50, inclusively.

Before providing a further description of the selection of the valid area of the blood smear 32 by means of the local frequency and the local average size, it shall also be noted that the following embodiments are based on the assumption, by way of example, that the pictures 36 represent the blood smear 32 with the same lateral accuracy in each case. However, this is not necessary. Potential differences in the lateral accuracy and/or the distance between pixels on the blood smear 32 might also be taken into account when determining the values of the local frequency and the local average size.

Figure 4A:
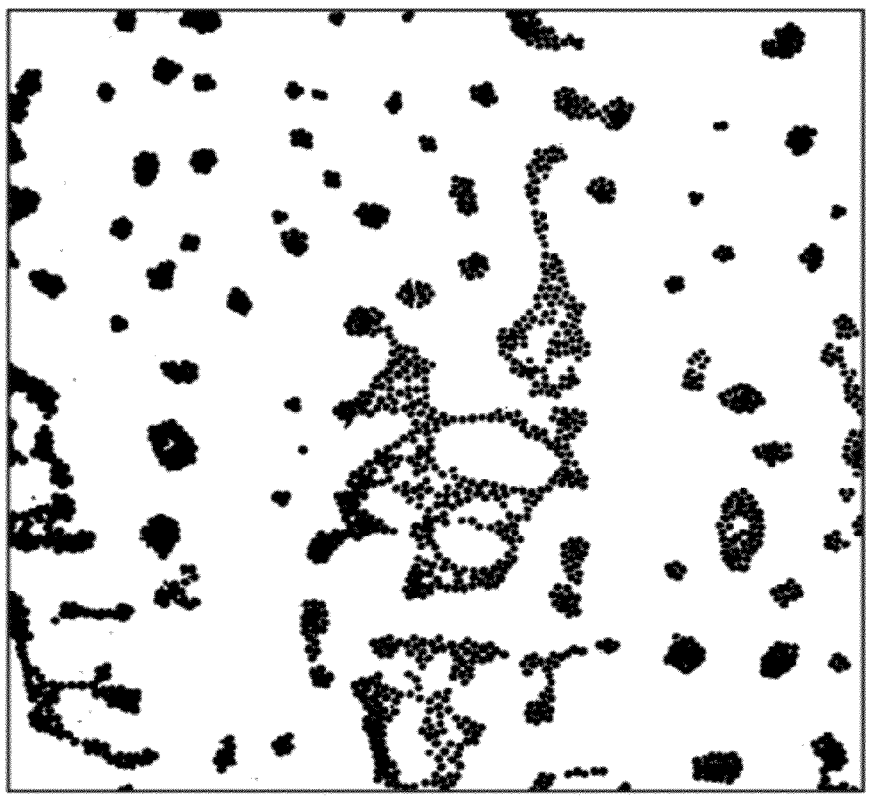
FIGS. 4a-c are representations of the pictures of FIGS. 3a-3c following classification of the pixels in terms of foreground and/or blood cells and background in accordance with an embodiment.
Figure 3A:
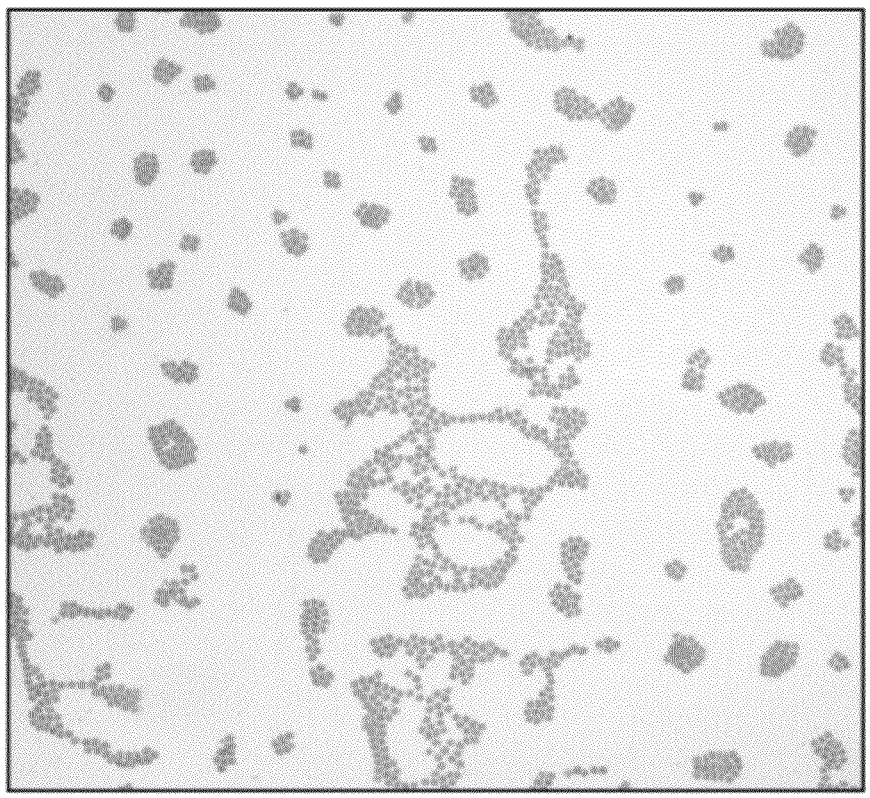
FIGS. 3a-c show exemplary pictures of different areas of a blood smear, FIG. 3a having a low cell density, FIG. 3b corresponding to a valid area, and FIG. 3c having a high cell density.
Figure 4B:
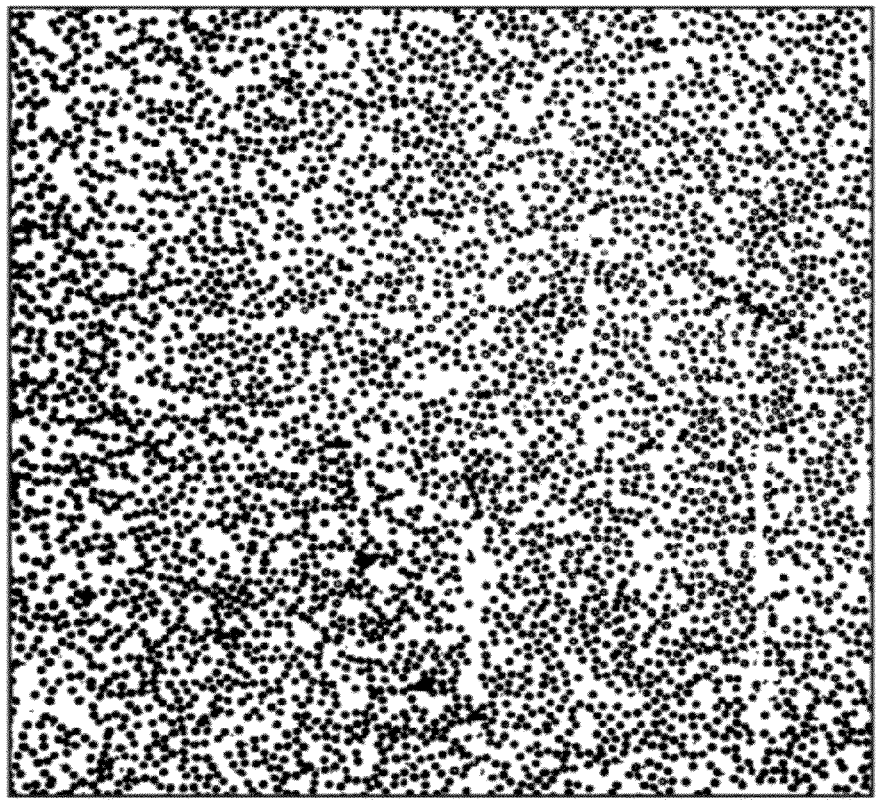
Figure 3B:
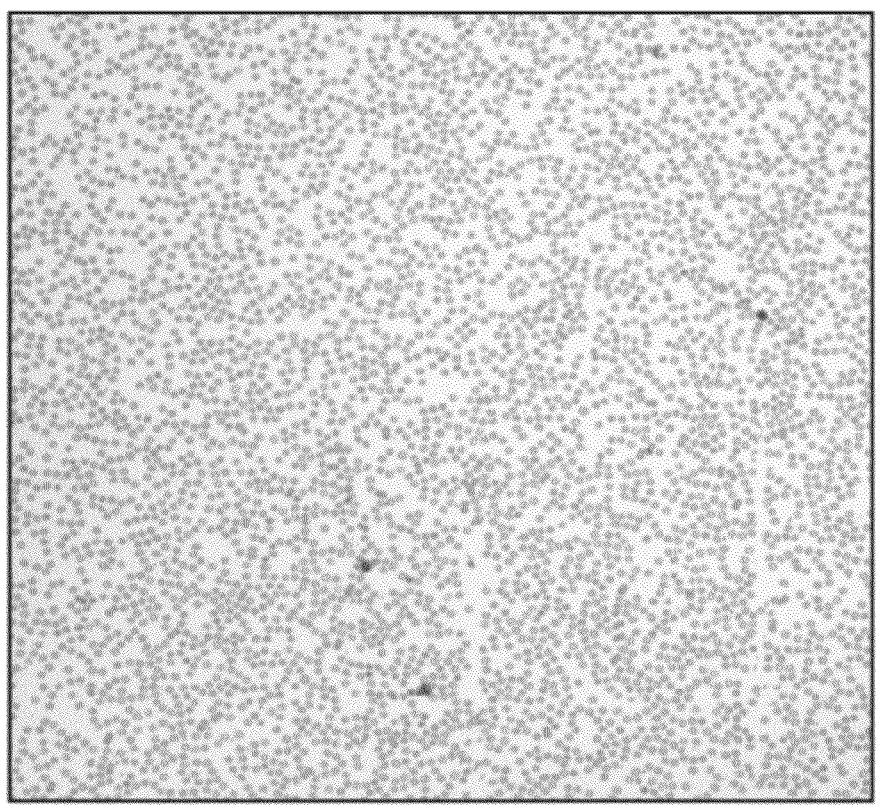
Figure 4C:
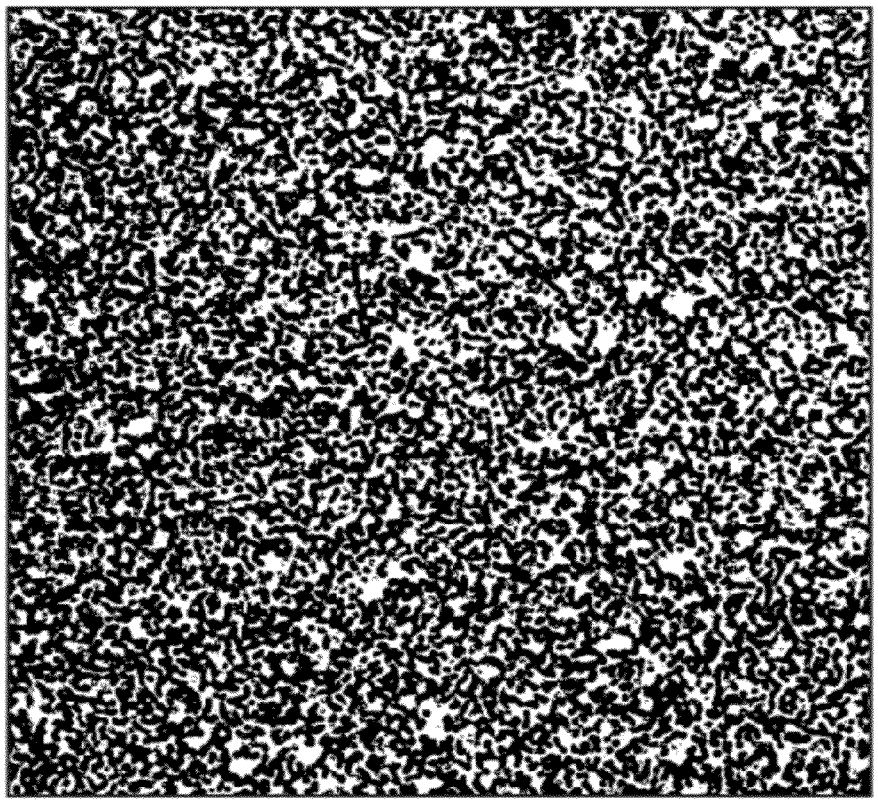
Figure 3C:
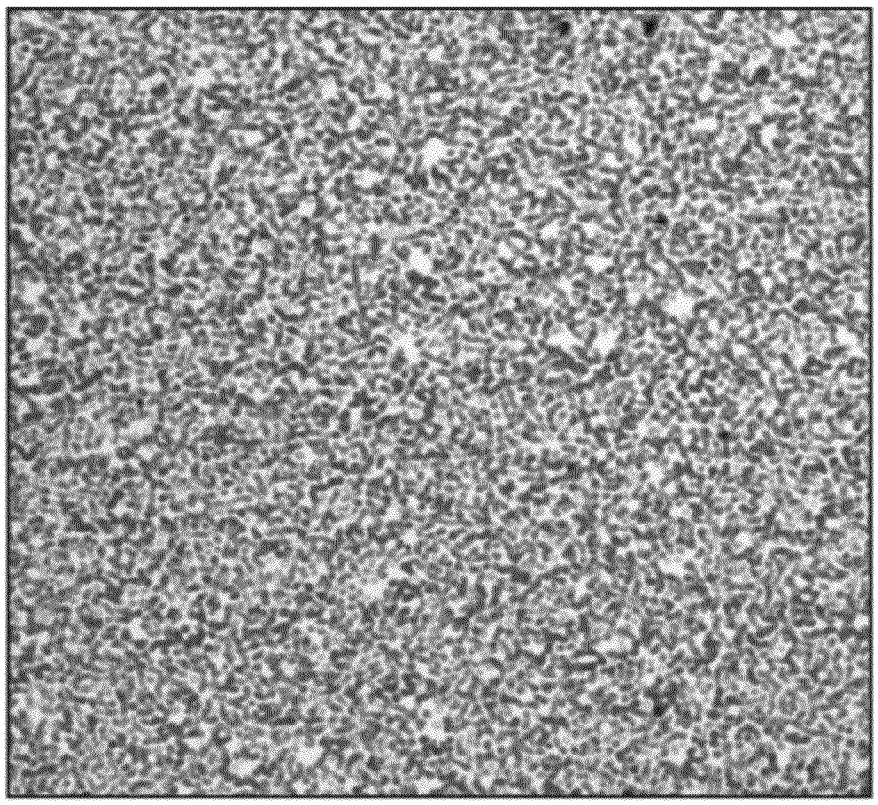

When the pairs of values of the local frequency $N_i$ and the local average size $A_i$ for the individual pictures i are plotted within a plane spanned by an axis 46 for the local accuracy N and an axis 48 for the local average size A, the corresponding points that are labeled with the picture index in FIG. 2 by way of example and are indicated by a x, typically lie along a track 50. Due to a property of the process of preparing a smear, the points along the track 50 are arranged essentially in that order which corresponds to the order of their arrangement along the direction 38 of the smear. In particular, on one end, the track starts with pairs of values of pictures wherein, as is indicated at 52, the number of pixel clusters per picture is still relatively small, since the blood cells have contracted into lumps, so that pixel clusters have a relatively large average size. Examples of a corresponding picture 36 of such an area of a blood smear and of the binary image 42 that results by way of example are shown in FIGS. 3a and 4a, respectively. This is followed by a portion 54, within which the blood cells are nicely separated from one another. In this portion 54, the number of pixel clusters per picture increases for some time while the average cluster size remains approximately the same. However, as is shown at 56, at some point the number of pixel clusters and/or blood cells in the pictures increases to such an extent that some pixel clusters and/or blood cells touch one another and unite to form larger clusters, and a little later, at 58, this effect even results in that the number of pixel clusters decreases, whereas the average size of the pixel clusters increases. Examples of a corresponding picture 36 from the area 58 and the binary image 42 that results, by way of example, are shown in FIGS. 3c and 4c, respectively. An ideal valid area is located roughly between the areas 54 and 56, or at the end of the area 54, and an example of this, and a corresponding picture 36 of such a valid area and the binary image 42 that results therefrom, for example, are shown in FIGS. 3b and 4c, respectively.

The selector 16 might be configured to geometrically determine the valid area from evaluating the track 50. To this end, the selector 16 might use the positions where the individual pictures are arranged, for example. In particular, the selector 16 might geometrically determine, from the track 50, the end of the area 54, or the transition between the areas 54 and 56, and might select that area as the valid area which corresponds to the picture that comes closest to this position of the track 50, or the position located between the two pictures that are closest to this position, such as by means of interpolation between the two positions.

A different approach that was used in the embodiments described below consists in that the selector 16 determines, for each pair of values $N_i$, $A_i$ a measure of suitability as a valid area, FIG. 2 indicating, at 60, the change of such a measure relative to the picture number, by way of example. As the valid area the selector 16 might use that area for which the measure is extremal. In FIG. 2, this is the case at 62, for example, which position roughly corresponds to the picture having the picture index 4. As the valid area, the selector 16 might also select a position between two closest pictures of the extreme point. This approach will be addressed in more detail below, which is why it will not be described in any more detail at this point.

Since an example of localization of a valid area of a blood smear was described above in more or less qualitative terms with regard to FIG. 2, a more or less mathematical description will be used below. Examples of a possible measure of suitability as a valid area will be provided, said measure depending on the local frequency and the local average size.

Let us contemplate a set of M images 36. For simplicity's sake it shall be assumed that said images 36 were obtained by means of systematically and completely scanning a slide. However, to accelerate the scanning process, arbitrary heuristics may be used in order to restrict the search space as is used for the evaluation to be described later on. While the pictures are taken, the slide is located on a stage, for example, which presents its content (the blood smear) to the optics of the microscope. Complete scanning is achieved in that the stage is moved, an image having a magnification factor of, e.g., 10 being obtained, and the position of the stage being stored until the entire slide has been captured in the pictures. For example, the stage defines a global coordinate system having x, y, and z axes. Each picture 36 of the blood smear 32 corresponds to the position where it was taken, and vice versa.

The localization described here is independent of any specific coloring. However, the coloring should effect a sufficiently large contrast between the background and the cells. For example, it is possible to use blood smears that were colored as specified by Pappenheim using MGG (May-Grünwald-Giemsa) solutions.

For such scanning, the $i^{th}$ image may be designated by $I_i$, whereas its corresponding position in slide coordinates is given by $p_i = (x_i, y_i, z_i)$. The superscript lettering of an image shall designate the color space to which it relates. Thus, the image $I_i^{HSV}$ represents the image $I_i$ in the HSV color space, and $I_i^{(s)}$ is to relate to its saturation channel, whereas $I_i^{(s)}(x, y)$ is to represent the value of an individual pixel at (x, y) within the plane referenced. For clarity's sake, the superscript notation relating to the color space is omitted when observing an RGB image.

The following steps are performed for each image $I_i$ of the sequence:

Conversion of $I_i$ to a cylindrical HSV representation: $I_i \to I_i^{HSV}$

Separation 46 of cells from the background. To this end, a binarization operator $B\{.\}$ is applied to the saturation channel $I^{(s)}$, which results in a threshold value $\tau_i$:

$$\tau_i = B\{I_i^{(s)}\}.$$

The binarization operator $B\{.\}$ may thus include, e.g., a threshold-value comparison with the saturation threshold value $\tau_i$, wherein pixels (x, y) having a saturation value $I^{(s)}$ of more than $\tau_i$ are interpreted as being pixels that represent the blood cells of interest, i.e. belong to the foreground.

Extraction 44 of the number $N_i$ of interconnected regions formed by an accumulation with a minimum of $A_{min}$ pixels in order to prevent the detection of smaller regions caused by dirt or noise on the slide or in the optical path. A region $R_j$ is defined by all of the neighboring pixels $p = (x, y)$ and $\tilde{p} = (\tilde{x}, \tilde{y})$ belonging to the foreground:

$$N_i = |\cup \{R_j : |R_j| \geq A_{min}\}|,$$

$$R_j = \{p, \tilde{p} : I_i^{(s)}(p) \geq \tau_i \wedge I^{(s)}(\tilde{p}) \geq \tau_i \wedge \|p - \tilde{p}\| \leq 1\}$$

The operator $|.|$ is to indicate the number of pixels belonging to a contiguous region. The operator $\|.\|$ is to indicate the lateral distance in units of a pixel repetition distance.

Extraction 44 of the surface area $A_j$ of the regions $R_j$ and/or the number of pixels of a specific region $R_j$ results in $$A_j = |\{R_j : |R_j| \geq A_{min}\}|, j = 1, \ldots, N_i$$

Calculation of the average area $\overline{A}_i$ from the areas $A_j$:

$$\overline{A}_i = \frac{1}{N_i} \sum_{j=1}^{N_i} A_j$$

Here, the mean value was used, but a different central tendency is also possible.

Calculation of the indicator function $\vartheta$ (i) as a measure of suitability as a valid area. $\vartheta$ (i) yields a characteristic value i* for the position $p_{i*}$ of the image i, and enables determination of parts of the valid region of the blood smear, which is thus a suitable starting point for subsequent determination of the WBC, for example.

Figure 5:
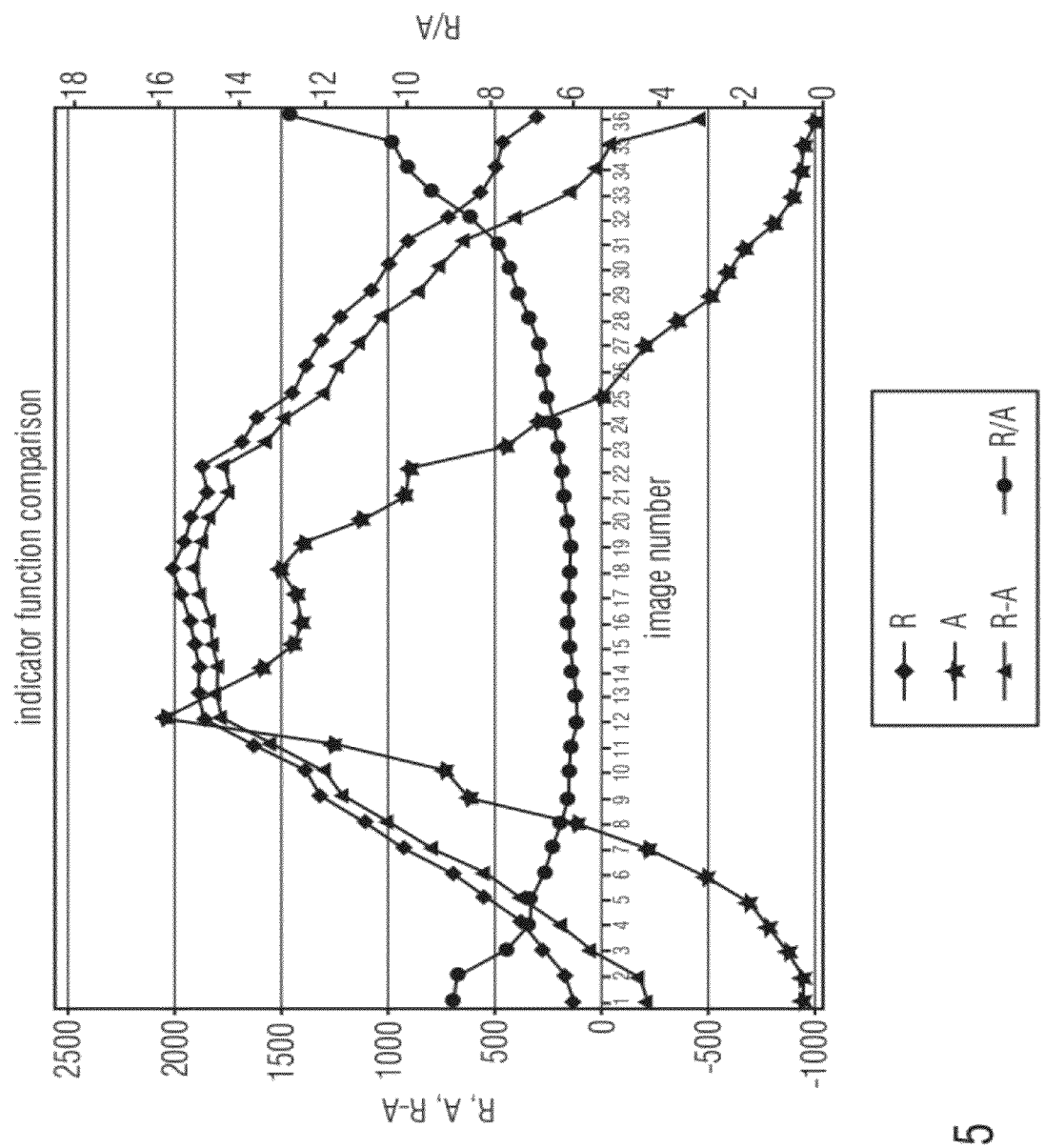
FIG. 5 shows a graph wherein, for exemplary scanning of a blood smear with 36 pictures at areas of the blood smear that are mutually offset in the direction of the smear, the lateral distributions of local frequency, of the local average size, and a measure of suitability as a valid area in accordance with two embodiments are plotted.
Figure 6A:
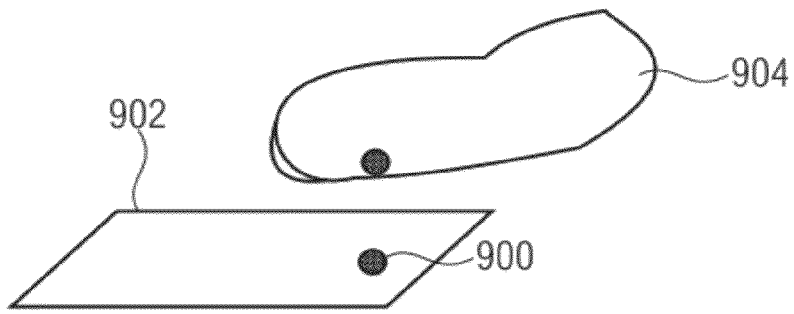
FIGS. 6a-d show schematic drawings for illustrating possible method steps for preparing a blood smear.
Figure 6B:
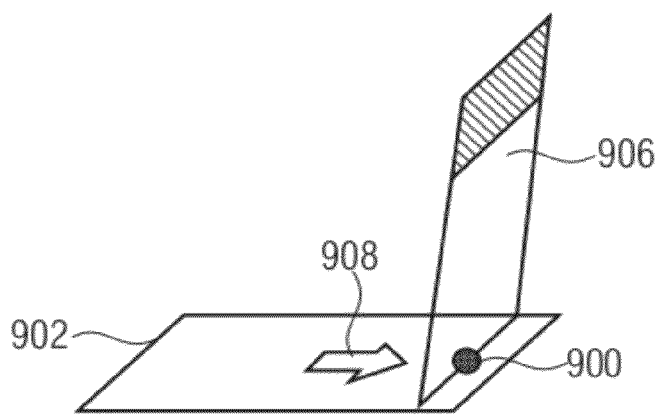
Figure 6C:
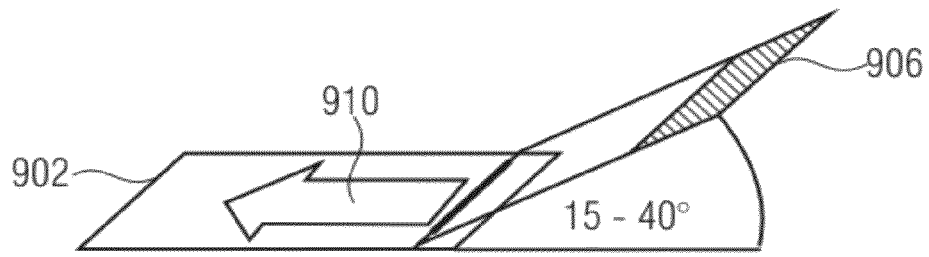
Figure 6D:
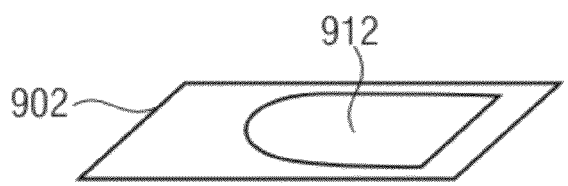

Two different indicator functions $\vartheta$ (i) based on $\overline{A}_i$ and $N_i$ will be examined in the following for the purpose of robust determination of the index i*, which corresponds to a position $p_{i*}$ in the valid region. This is why FIG. 5 represents four function graphs of an exemplary slide, which indicate the functions $\overline{A}_i$, $N_i$ and the indicator functions $\vartheta$ (i)=$N_i$-$\overline{A}_i$ and $$\vartheta(i) = \frac{N_i}{\overline{A}_i}.$$

The position p of the valid region is then given by the global maximum i* of the indicator values $\vartheta$ (i). The indicator function $\vartheta$ (i)=$N_i$-$\overline{A}_i$ provides good results, but does not sufficiently take into account the average cluster size and results in a global maximum for the image 18, whereupon the expert selected the valid region for the images 11 to 14. The indicator function $\vartheta$ (i)=$N_i/\overline{A}_i$ attaches greater importance to the cluster size, has its maximum in the image 12 and is thus a more reliable quality function, wherein the characteristic index i* is given by the global maximum of $\vartheta$ (i).

The position p* of the valid region is then given by the global maximum i* of the indicator value $\vartheta$ (i). The position $p_{i*}$, which corresponds to the index i*, is bound to be part of the valid region of the blood smear. Thus, it may be used as the starting point for subsequent determination of the WBC.

In yet other words, M pictures of ten-fold magnification of the entire blood smear of the slide may be detected in a digital form in order to determine a valid area, the position Pi of the $i^{th}$ picture being stored. Subsequently, the pictures are evaluated as follows by means of image processing algorithms:

The following individual steps are performed for each image $m_i$ of the M pictures:
1. Transforming the RGB image to the HSV color space.
2. Automatic binarization such as in accordance with the article by Otsu et al., A Threshold Selction Method from Gray-Level Histograms, IEEE Transaction on Systems, MAN and Cybernetics, No. 1, January 1979, pp. 62-64, such as by means of the saturation channel (S channel).
3. Determining the number $N_i$ of contiguous regions that are defined as foreground in the binary image.
4. Determining the surface area $F_j$, j=1–$N_i$ of the above-mentioned contiguous regions (in pixels).
5. Calculating the average area content C, of all of the surface areas $F_j$.
6. Calculating the difference D(i) between the number of regions $N_i$ and the average area content $C_i$: D(i)=$N_i$–$C_i$.

A position P* of the valid area of the blood smear results from the global maximum i* of the function D(i). The image position $P^*_i$ associated with the index i* is bound to be part of the valid area and serves as a starting point for subsequent creation of the differential blood count.

Within the context of automatic creation of a differential blood count, reliable detection of the valid area is indispensable. The above embodiments provide the foundation for further steps in an automatic differential blood count analysis. In the case of manual creation, this area is initially be located on the slide, which initially entails an increased amount of time involved. In addition, this may result in variations. For example, the area selected will not always be the ideal area. In turn, said variations have a direct influence on the result of the differentiation and thus possibly also on the final diagnosis, which relies on this distribution. Automatic recognition of the valid area in accordance with one of the above embodiments also offers the possibility of recognizing poorly or insufficiently prepared smears and of thus increasing the quality of the differential blood count analysis.

To evaluate the accuracy of the presented approach to localize the valid area on blood smears, several sets of pictures were taken and analyzed. The pictures were taken while using the above-mentioned HemaCAM system. All of the slides but one were prepared using a slide preparation device and colored using a coloring device. Each of the sets of images consists of 50 adjacent pictures that were taken along the center line of the longitudinal direction of the blood smear, which represents the major part of the linear extension of a blood smear—starting at that end of the blood smear at which the cell density is low. These sets of pictures were evaluated by an experienced hematologist and were analyzed by means of the algorithm so as to find those images that depict the valid region. The results are listed in Table I for comparative purposes.

In most sets of pictures, the expert found more than one image depicting the valid area of the blood smear, whereas the algorithm provided only one image number. Even at set 22, where a manually smeared and colored slide was analyzed, and where only one image shows the valid area, for each set of pictures the algorithm matched one of the image numbers selected by the expert.

TABLE 1

| Set of Pictures | Hematologist | Algorithm |
|---|---|---|
| 1 | 9-12 | 9 |
| 2 | 17-22 | 21 |
| 3 | 14-17 | 15 |
| 4 | 16-19 | 18 |
| 5 | 26, 27 | 27 |
| 6 | 13-15 | 13 |
| 7 | 17-19 | 19 |
| 8 | 17-19 | 19 |
| 9 | 16-20 | 20 |
| 10 | 17-20 | 19 |
| 11 | 16-20 | 20 |
| 12 | 15-19 | 18 |
| 13 | 8-10 | 10 |
| 14 | 16-20 | 19 |
| 15 | 24-27 | 25 |
| 16 | 14-17 | 14 |
| 17 | 12, 13 | 11 |
| 18 | 10-15 | 10 |
| 19 | 17-25 | 21 |
| 20 | 10-15 | 13 |
| 21 | 11-14 | 13 |
| 22 | 20 | 20 |

The above-mentioned embodiments might be employed, for example, in the HemaCAM (registered trademark) system of the Fraunhofer-Gesellschaft. This system was developed for automated examination of blood smears so as to assist a doctor in their WBC-based diagnosis. The system comprises a Zeiss Axio Imager M1 having a table automatically adjustable in height (z axis), a Zeiss Achroplan Objective having a 10-fold magnification, a 1-fold tube adaptor, a CCD camera AVT Pike F-100C, and LED illumination. Moreover, the system comprises a Marzhauser stage configured for several slides in order to move the slide in two directions (x and y axes) below the objective. The HemaCAM software including the user-interface, hardware-control and image-processing algorithms came out on top.

In other words, robust detection and accurate segmentation of the white blood cells (leucocytes) in colored blood smears of peripheral blood provides the basis for fully-automatic image-based creation of the so-called differential blood count in connection with medical laboratory diagnostics (so-called computer-assisted microscopy—CAM). Particularly in order to localize the blood cells and to segment the cells it is useful to detect the valid region (the work area) of the blood smear wherein the cells are separated for the most part and do not influence one another. The previous embodiments provide an approach to localize the valid region on colored blood smears. In some embodiments, several pictures are taken of the blood smear and analyzed as follows. Following binarization of each picture taken while using the threshold obtained, for example, by means of the Otsu algorithm, the regions in the resulting images are analyzed. The number of regions and their average sizes are stored for each image and compared with one another. That image that shows the valid area of the blood smear has a large number of areas and a small average area size. The method may be evaluated using several sets of pictures taken of different blood smears. Each set of pictures may be analyzed using one of the algorithms introduced, and the results may be verified by an experienced hematologist. The results of the evaluation indicate the possibilities of the approach presented.

Even though some aspects were described in connection with an apparatus, it is understood that said aspects also represent a description of the corresponding method, so that a block or a component of an apparatus is also to be understood as a corresponding method step or as a feature of a method step. By analogy therewith, aspects that were described in connection with or as a method step also represent a description of a corresponding block or detail or feature of a corresponding apparatus.

Depending on specific implementation requirements, embodiments of the invention may be implemented in hardware or in software. Implementation may be performed using a digital storage medium, for example a floppy disc, a DVD, a Blu-ray disc, a CD, a ROM, a PROM, an EPROM, an EEPROM, or a flash memory, a hard disc or any other magnetic or optical memory which has electronically readable control signals stored thereon that may cooperate, or indeed do cooperate, with a programmable computer system such that the respective method is performed. This is why the digital storage medium may be computer-readable. Some embodiments in accordance with the invention thus include a data carrier having electronically readable control signals that are capable of cooperating with a programmable computer system such that any of the methods described herein is performed.

Generally, embodiments of the present invention may be implemented as a computer program product having a program code, the program code being operative to perform any of the methods when the computer program product runs on a computer. The program code may also be stored on a machine-readable carrier, for example.

Other embodiments include the computer program for performing any of the methods described herein, the computer program being stored on a machine-readable carrier.

In other words, an embodiment of the inventive method thus is a computer program having a program code for performing any of the methods described herein, when the computer program runs on a computer. A further embodiment of the inventive methods thus is a data carrier (or a digital storage medium or a computer-readable medium) on which the computer program for performing any of the methods described herein is recorded.

A further embodiment of the inventive method thus is a data stream or a sequence of signals representing the computer program for performing any of the methods described herein. The data stream or the sequence of data may be configured, e.g., to be transferred via a data communication link, for example via the internet.

A further embodiment includes a processing means, for example a computer or a programmable logic device, configured or adapted to perform any of the methods described herein.

A further embodiment includes a computer on which the computer program for performing any of the methods described herein is installed.

In some embodiments, a programmable logic device (e.g. a field-programmable gate array, an FPGA) may be used for performing some or all of the functionalities of the methods described herein. In some embodiments, a field-programmable gate array may cooperate with a microprocessor to perform any of the methods described herein. In some embodiments, the methods are generally performed by any hardware device. The latter may be a universally employable hardware such as a computer processor (CPU) or a hardware specific to the method, such as an ASIC, for example.

The above-described embodiments merely represent an illustration of the principles of the present invention. It is to be understood that modifications and variations of the arrangements and details described herein will be appreciated by other persons skilled in the art. This is why it is intended that the invention be limited only by the scope of the following claims rather than by the specific details that were presented herein by means of the description and the explanation of the embodiments.

A signal coded in accordance with the invention, such as an audio or a video signal, for example, may be stored on a digital storage medium or may be transmitted, for example, on a transmission medium such as a wireless transmission medium or a wired transmission medium, e.g. the internet.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

The invention claimed is:

1. An apparatus for localizing a valid area of a blood smear, comprising
a provider for providing at least one picture of the blood smear;
a classifier for classifying pixels of the at least one picture at least into first pixels, which represent blood cells, and second pixels, which do not represent the blood cells;
a selector for selecting an area of the blood smear as the valid area on the basis of a local frequency of contiguous pixel clusters of at least $A_{min}$ first pixels, $A_{min}$ being a minimum threshold value of a number of first pixels of a pixel cluster, and of a local average size of the pixel clusters for laterally distributed areas of the blood smear.

2. The apparatus as claimed in claim 1, wherein the selector is configured to select, on the basis of the local frequency and the local average size of the pixel clusters, a locally varying measure of suitability as a valid area for the laterally distributed areas of the blood smear, and to make the selection such that that area wherein the laterally varying measure is extremal will be selected as the valid area among the laterally distributed areas.

3. The apparatus as claimed in claim 2, wherein the selector is configured such that the laterally varying measure depends on the local frequency and on the local average size for the laterally distributed areas in accordance with a function that is either strictly monotonically decreasing for the local frequency and strictly monotonically increasing for the local average size, or is strictly monotonically increasing for the local frequency and strictly monotonically decreasing for the local average size.

4. The apparatus as claimed in claim 2, wherein the selector is configured such that it determines the laterally varying measure for each of the laterally distributed areas on the basis of a quotient of or a difference between the local frequency and the local average size for the respective one of the locally distributed areas.

5. The apparatus as claimed in claim 2, wherein the selector is configured such that it determines the laterally varying measure for each of the laterally distributed areas to be k(N−A), wherein k is a constant different from zero, N is the number of pixel clusters within the respective area of the laterally distributed areas, and A is the average number of pixels of the pixel clusters within the respective area of the laterally distributed areas, the laterally distributed areas being equal in size.

6. The apparatus as claimed in claim 2, wherein the selector is configured such that it determines the laterally varying measure for each of the laterally distributed areas to be k(N/A), wherein k is a constant different from zero, N is the number of pixel clusters within the respective area of the laterally distributed areas, and A is the average number of pixels of the pixel clusters within the respective area of the laterally distributed areas, the laterally distributed areas being equal in size.

7. The apparatus as claimed in claim 1, wherein the provider is configured to provide several pictures of the blood smear, which represent portions of the blood smear that are laterally offset from one another.

8. The apparatus as claimed in claim 7, wherein the selector is configured such that each picture is associated with a different one of the laterally distributed areas, and is configured to determine, for each picture, the local frequency on the basis of a number of the contiguous pixel clusters in the respective picture, and the local average size on the basis of the number of pixels per pixel cluster.

9. The apparatus as claimed in claim 7, wherein the provider is configured to provide the pictures with a 10-fold or a 20-fold magnification or any magnification in between at a resolution of 400×400 pixels, 2000×2000 pixels or any resolution in between, the selector being configured such that $A_{min}$ ranges from 10, inclusively, to 50, inclusively.

10. The apparatus as claimed in claim 1, wherein the classifier is configured to perform the classification on the basis of a subdivision of a color space into at least a first portion, which is associated with the first pixels, and a second portion, which is associated with the second pixels.

11. The apparatus as claimed in claim 1, wherein the classifier is configured such that it distinguishes between pixels representing red blood cells and pixels representing white blood cells, and classifies as the first pixels only those pixels among same which represent the red blood cells.

12. A method of localizing a valid area of a blood smear, comprising
providing at least one picture of the blood smear;
classifying pixels of the at least one picture at least into first pixels, which represent blood cells, and second pixels, which do not represent the blood cells;
selecting an area of the blood smear as the valid area on the basis of a local frequency of contiguous pixel clusters of at least $A_{min}$ first pixels, $A_{min}$ being a minimum threshold value of a number of first pixels of a pixel cluster, and of a local average size of the pixel clusters for laterally distributed areas of the blood smear.

13. A non-transitory computer readable medium including a computer program for performing a method of localizing a valid area of a blood smear, when the computer program is executed by a processor, said method comprising
providing at least one picture of the blood smear;
classifying pixels of the at least one picture at least into first pixels, which represent blood cells, and second pixels, which do not represent the blood cells;
selecting an area of the blood smear as the valid area on the basis of a local frequency of contiguous pixel clusters of at least $A_{min}$ first pixels, $A_{min}$ being a minimum threshold value of a number of first pixels of a pixel cluster, and of a local average size of the pixel clusters for laterally distributed areas of the blood smear.

* * * * *